US007868201B2

(12) United States Patent
Zhan et al.

(10) Patent No.: US 7,868,201 B2
(45) Date of Patent: Jan. 11, 2011

(54) PROCESS AND CATALYST FOR OXIDATION OF HYDROCARBONS

(75) Inventors: Bi-Zeng Zhan, El Cerrito, CA (US);
Bjorn Moden, Berkeley, CA (US);
Jihad Dakka, Whitehouse Station, NJ (US); Jose Santiesteban, Baton Rouge, LA (US); Sebastian C. Reyes, Branchburg, NJ (US); Enrique Iglesia, Moraga, CA (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 0 days.

(21) Appl. No.: 11/173,594

(22) Filed: Jul. 1, 2005

(65) Prior Publication Data
US 2007/0004944 A1 Jan. 4, 2007

(51) Int. Cl.
C07C 51/00 (2006.01)
C07C 45/00 (2006.01)
C07C 27/10 (2006.01)
B01J 29/06 (2006.01)
B01J 29/068 (2006.01)
B01J 29/072 (2006.01)

(52) U.S. Cl. .................. 562/412; 562/417; 562/504; 562/523; 562/527; 562/531; 562/538; 562/542; 562/549; 568/320; 568/357; 568/375; 568/376; 568/398.8; 568/399; 568/431; 568/469.9; 568/475; 568/815; 568/821; 568/836; 568/910; 568/910.5; 502/64; 502/66; 502/71

(58) Field of Classification Search .................. 562/412, 562/417, 504, 523, 527, 531, 538, 542, 549; 568/320, 357, 399, 431, 375, 376, 398.8, 568/469.9, 475, 815, 821, 836, 910, 910.5
See application file for complete search history.

(56) References Cited

U.S. PATENT DOCUMENTS

| | | | | |
|---|---|---|---|---|
| 3,557,024 | A * | 1/1971 | Young et al. | 502/66 |
| 4,097,543 | A | 6/1978 | Haag et al. | |
| 4,299,990 | A | 11/1981 | Tummes et al. | |
| 4,918,249 | A * | 4/1990 | Durante et al. | 568/910 |
| 5,426,237 | A | 6/1995 | Murahashi et al. | |
| 5,633,417 | A | 5/1997 | Beck et al. | |
| 6,548,718 | B2 * | 4/2003 | Murray et al. | 568/910.5 |
| 6,670,509 | B1 * | 12/2003 | Kurek et al. | 568/320 |
| 6,852,893 | B2 | 2/2005 | Kuhnle et al. | |
| 7,081,552 | B2 * | 7/2006 | Pirutko et al. | 568/354 |
| 2005/0065378 | A1 | 3/2005 | Bosch et al. | |

OTHER PUBLICATIONS

Bai, Zilong et al.; "Oxidation of alkanes over zeolite-encapsulated vanadium"; 2002, *Cuihua Xuebao*, vol. 23, No. 1, pp. 29-32, abstract only, 1 page.

Cook, Bruce R. et al.; "Shape Selective Alkane Hydroxylation by Metalloporphyrin Catalysts"; Apr. 1986, *J. Am. Chem. Soc.* vol. 108, pp. 7281-7286.

Hari, P.R. et al.; "Oxyfunctionalization of Alkanes with $H_2O_2$ catalysed by Vanadium Silicates", May 1992, *J. Chem. Soc.*, pp. 1245-1246.

Herron, Norman et al.; "A Highly Selective Zeolite Catalyst for Hydrocarbon Oxidation. A Completely Inorganic Mimic of the Alkane w-Hydroxylases"; 1987, *J. Am. Chem. Soc.*, vol. 109, pp. 2837-2839.

Herron, Norman; The Selective Partial Oxidation of Alkanes using Zeolited based Catalysts. A completely inorganic cytochrome P450 mimic; Apr. 1989, *New Journal of Chemistry*, vol. 13, No. 10-11, pp. 761-766.

Ichikawa, Maseru et al.; "Ship-in-Bottle Synthesis of Sterically Crowded Fe-Phthalocyanines in NaY Zeolite Hosts and Their Catalytic Behavior in Regioselective Oxidation of Alkanes"; Jun. 1990, *Proceedings of the International Symposium on Chemistry of Microporous Crystals*, vol. 60, pp. 335-342.

Labinger, Jay A.; "Selective alkane oxidation: hot and cold approaches to a hot problem", Mar. 2004, *Journal of Molecular Catalysis A*, vol. 220, pp. 27-35.

McCusker L.B. et al.; "Nomenclature of structural and compositional characteristics of ordered microporous and mesoporous materials with inorganic hosts"; 2001, *Pure and Applied Chemistry*, vol. 73, pp. 381-394.

Moden, Bjorn et al.; "Structural and Functional Characterization of Redox Mn and Co Sites in AlPO Materials and Their Role in Alkane Oxidation Catalysis", Feb. 2004, *J. Phys. Chem. B*, vol. 108, pp. 5552-5563.

Tatsumi, Takashi et al.; Probable Mechanism for Alkane Oxidation with $H_2O_2$ over VS-2; 1998, *Res. Chem. Intermed.* vol. 24, No. 5, pp. 529-540.

(Continued)

*Primary Examiner*—Rosalynd Keys
(74) *Attorney, Agent, or Firm*—Robert A. Migliorini

(57) ABSTRACT

A process for the oxidation of hydrocarbons comprises contacting the hydrocarbon with an oxygen-containing gas in the presence of a catalyst comprising a microporous solid support, preferably a zeolite, having from 8- to 12-ring open windows and comprising non-framework metal cations selected from manganese, iron, cobalt, vanadium, chromium, copper, nickel, and ruthenium, and mixtures thereof, providing that the oxygen-containing gas does not contain significant amounts of added hydrogen. The catalyst is novel and forms part of the invention.

The process may be used for oxidation of alkanes, cycloalkanes, benzene and alkylbenzenes, and is suitable for use in regioselective terminal oxidation of straight chain alkanes and for selective oxidation/separation of p-dialkylbenzenes from an alkylbenzene mixture, for example, p-xylene from an isomeric mixture of xylenes.

44 Claims, 3 Drawing Sheets

OTHER PUBLICATIONS

Tatsumi, T. et al.; "Alkane Oxidation on Vanadium Silicalite Compared to Titanium Silicalite"; 1996, *American Chemical Society*; chapter 28, pp. 376-382.

Thomas, John M. et al.; "Molecular-sieve catalysts for the selective oxidation of linear alkanes by molecular oxygen", Mar. 1999, *Nature*, vol. 398, pp. 227-230.

Tolman, Chadwick A. et al.; "The Oxidation of Organic Compounds by Metal Complexes in Zeolites"; Mar. 1987, *Proceedings of the Fifth Annual IUCCP Symposium*, pp. 293-303.

Zhou, Ying-fei et al.; "Regioselectivity in catalytic oxidation of alkanes using zeolite-encapsulated catalyst"; 2003, *Casreact*, vol. 140, abstract 28740, 1 page.

* cited by examiner

Homogeneous oxidation of n-hexane: ROOH (▲), ROH+R=O (●), and acids (♦, including hexanoic acid and other acids via C-C bond cleavage)

ROOH (▲), ROH+R=O (●), and acids (◆)

Terminal regioselectivity of n-hexane oxidation vs. reaction time: homogeneous oxidation (▲), Mn-ZSM-57 (●), and Mn-ZSM-5 (◆);

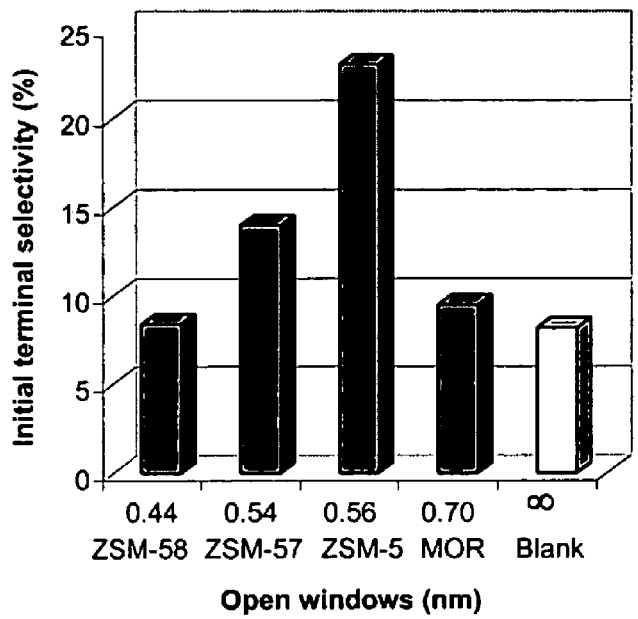
Figure 4
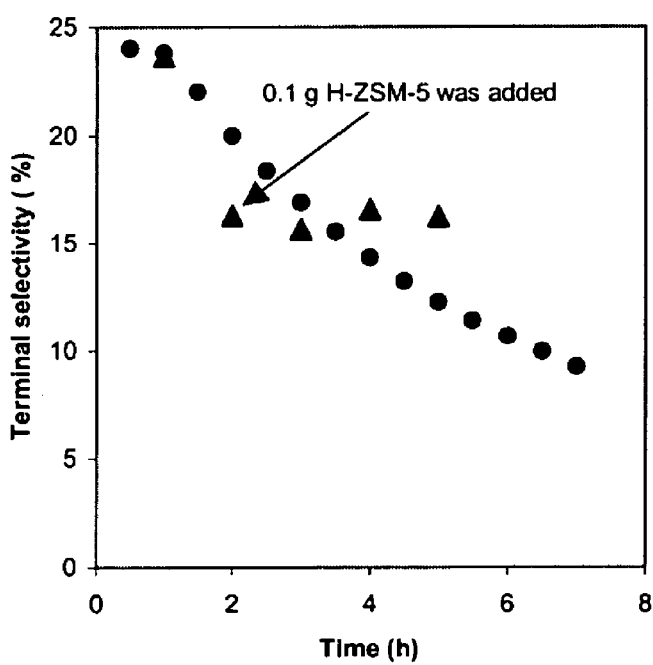
Figure 5: terminal selectivity of n-hexane oxidation using combination of Mn- and H-ZSM-5

PROCESS AND CATALYST FOR OXIDATION OF HYDROCARBONS

BACKGROUND OF THE INVENTION

This invention relates to a process and catalyst for the oxidation of hydrocarbons and, in one preferred embodiment, for selective production of alkanes that are terminally substituted with oxygenated moieties, for example, to the production of aldehydes, 1-alkanols and/or 1-carboxylic acids from the corresponding alkane, most preferably straight-chain alkane.

Oxidation of hydrocarbons to produce oxygenated products has been carried out using a number of techniques, including the use of various catalysts and oxidizing agents. Typically, however, oxidation of straight chain alkanes produces a mixture of oxygenated products, with the oxidation taking place predominantly at non-terminal carbon atoms in the chain. For instance, oxidation of n-hexane typically primarily produces a mixture of 2- and 3-hexanols, together with the corresponding ketones. Aliphatic aldehydes, such as valeraldehyde (pentanal), caproaldehyde (hexanal), enanthaldehyde (heptanal), caprylaldehyde (ocatanal), capraldehyde (decanal), and the like, are typically produced, on the other hand, by hydroformylation of an olefin, i.e. by reacting an olefin having one less carbon atom than the desired aldehyde with hydrogen and carbon monoxide in the presence of a suitable catalyst. However, these processes are expensive, involving complicated chemistry and expensive feeds. In addition, hydroformylation of olefins first requires oligomerization to form the longer chain olefins. Primary alcohols are typically currently produced by olefin hydroformylation, ester hydrogenation or olefin hydration using hydrogen peroxide and boric acid (see, e.g., Zweifel et al., *J. Am. Chem. Soc.* 89, 291 (1967).

Selective oxidation of alkanes, especially straight-chain alkanes, is a less than straightforward operation. Enzymes (e.g. ω-hydroxylase) with non-heme iron active centers have been found to catalyze the oxidation of alkanes using $O_2$ with high terminal regioselectivity, apparently because proteins near active centers lead to selective docking and binding. See, for instance, Hamberg et al., in Molecular Mechanisms of Oxygen Activation (ed. Hayaishi, O.) 24-52 (Academic Press, New York, 1974). Many recent studies have attempted to mimic these unique properties. About 20% terminal regioselectivities were reported for linear alkanes on sterically-hindered Mn(III) active centers in metalloporphyrins [Cook et al., *J. Am. Chem. Soc.* 108, 7281 (1986)]. As described in that publication, n-hexane oxidation by iodosobenzene (PhIO) oxidant on 5,10,15,20-tetrakis(2',4',6'-triphenylphenyl)-porphyrinato-manganese(III)acetate [(MnTTPPP (OAc)] catalysts gave 19% 1-hexanol among all hexyl-alcohols. The corresponding primary selectivity index ($k_{prim}/k_{sec}$; defined as the ratio of primary to secondary products normalized by the number of each type of C—H bonds) was 0.31. Inorganic solids that catalyze oxidation of alkanes to alcohols, ketones, and acids using $O_2$ remain a significant challenge.

Some research has been carried out on oxidation of alkanes using zeolites containing metallic components. Regioselective oxidation to primary substituted oxygenated compounds was achieved in some cases. For instance, Tatsumi et al., *American Chemical Society Symposium Series* 638:374 (1996) and *Res. Chem. Intermed.* 24:529 (1998) investigated oxidation of n-hexane and cyclohexane with the vanadium-containing zeolite VS-2 using hydrogen peroxide as the oxidant, and found that the catalyst was suitable both for oxidation of n-hexane, with some selectivity towards terminally substituted compounds, and for oxidation of cyclohexane. This was contrasted by the authors, however, to previous work by others on titanium zeolite analogs TS-1 and TS-2, which gave only secondary alcohols and ketones from the oxidation of n-hexane using hydrogen peroxide.

Herron et al. [*J. Am. Chem. Soc.* 109:2837 (1987)] found appreciable terminal oxidation of n-pentane, n-octane and n-decane using zeolite 5A ion exchanged with iron and with palladium. Here the oxidant was a mixture of hydrogen and oxygen, which formed hydrogen peroxide in situ. Some work was also carried out with similar catalysts using zeolite ZSM-5. Herron [*New J. Chem.* 13:761 (1989)] demonstrated good results of this type using a ZSM-5 zeolite containing only iron, with hydrogen peroxide as the oxidant. Tolman et al. [Proc. Ann. IUCCP Symposium (1987); Martell, ed.] also conducted work using a mixture of hydrogen and oxygen as the oxidant. Thomas et al. [*Nature*, 398, 227 (1999)] describe oxidation of n-hexane and n-octane with dry air using aluminophosphate molecular sieves [AlPO materials] conaining $Co^{+3}$ or $Mn^{+3}$ ions as part of the framework. The authors claimed to have achieved as high as 60+% terminal oxidation products (alcohol, aldehyde, and carboxylic acid combined, with the acid predominating) from n-hexane and n-octane with one of their catalysts, MnAlPO18 (which has 8-ring open windows).

Demonceau et al. [*J. Molec. Catal.* 49, L13 (1988)] found that homogeneous sterically-hindered Rh 2,4-dichloro-3,5-dinitrobenzoic carboxylate complexes gave modest terminal regioselectivities (31%, $k_{prim}/k_{sec}$=0.60) for carbene insertion into C—H bonds in n-hexane. Recently, terminal regioselectivity was also reported in borylation of saturated alkanes, in which Bis(pinacolato)-diborane ($B_2pin_2$) or pinacolborane (HBpin) with some specificity with terminal C—H bonds in alkanes on Rh complexes with bulky ligands (Cp*Rh ($\eta^4$-$C_6Me_6$)) [Chen et al., *Science* 287, 1995 (2000)]. For example, n-octane reactions with HBpin led to n-octyl-1-Bpin, which was obtained with 65% yield after reaction for 14 hours.

BRIEF SUMMARY OF THE INVENTION

In general, this invention comprises a process for the oxidation of hydrocarbons comprising contacting the hydrocarbon with an oxygen-containing gas in the presence of a catalyst comprising a microporous solid support having from 8- to 12-ring open windows and comprising non-framework metal cations selected from manganese, iron, cobalt, vanadium, chromium, copper, nickel, and ruthenium, and mixtures thereof, providing that the oxygen-containing gas does not contain significant amounts of added hydrogen.

In one preferred embodiment, the invention comprises a process for oxidation of straight or branched-chain alkanes to form a product comprising one or more of terminal alcohols, aldehydes, carboxylic acids and ketones comprising contacting the alkane with a catalyst comprising a microporous solid support having 10-ring open windows and comprising non-framework metal cations selected from manganese, iron, cobalt, vanadium, chromium, copper, nickel, and ruthenium, and mixtures thereof, providing that the oxygen-containing gas does not contain significant amounts of added hydrogen.

In another embodiment the invention comprises a process for oxidation of cyclic saturated or unsaturated hydrocarbons to form a product comprising the corresponding alcohol, ketone or acid, comprising contacting the hydrocarbon with an oxygen-containing gas in the presence of a catalyst comprising a microporous solid support having from 8- to 12-ring open windows and comprising non-framework metal cations selected from manganese, iron, cobalt, vanadium, chromium, copper, nickel, and ruthenium, and mixtures thereof, providing that the oxygen-containing gas does not contain significant amounts of added hydrogen.

In yet another embodiment the invention comprises a process for selectively oxidizing a para-dialkylbenzene to form a product comprising one or more oxygenated derivatives thereof comprising contacting the dialkylbenzene with a catalyst comprising a microporous solid support having 10-ring open windows and comprising non-framework metal cations selected from manganese, iron, cobalt, vanadium, chromium, copper, nickel and ruthenium, and mixtures thereof, providing that the oxygen-containing gas does not contain significant amounts of added hydrogen.

In another aspect the invention comprises an oxidation catalyst comprising a microporous solid support having 10-ring open windows, comprising from about 0.01 to about 20 wt. %, preferably from about 0.1 to about 10 wt. %, most preferably from about 0.5 to about 5 wt. %, of non-framework manganese cations.

Other aspects of the invention will be apparent from the description that follows.

BRIEF DESCRIPTION OF THE DRAWINGS

FIG. 4 is a comparison of intrinsic terminal regioselectivity of n-hexane oxidation on various manganese-containing zeolite catalysts, and without a catalyst.

FIG. 5 depicts terminal selectivity of n-hexane oxidation using a combination of Mn- and H-ZSM-5.

DETAILED DESCRIPTION OF THE INVENTION

Figure 1A:
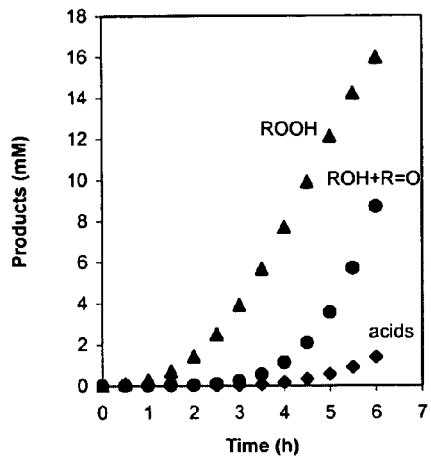
FIGS. 1a and 1b depict results of the homogeneous oxidation of n-hexane carried out in the absence of a catalyst of the invention.

The prior art processes discussed in the introductory sections above use, with one exception, hydrogen peroxide—either introduced as a feed or generated in situ—as the oxidizing agent for regioselective oxidation of alkanes and of cycloalkanes. However, while hydrogen peroxide is useful in a small number of commercial processes such as the production of propylene oxide or hydroquinone and water treatments, its use in commercial installations is less desirable because it requires costly on-purpose synthesis and elaborate handling techniques for safe operation. The present process does not use hydrogen peroxide, and thus provides advantages over most of the prior art discussed above. Thomas et al. do disclose a process in which air is the oxidant. However, the Thomas et al. catalyst is one in which manganese or cobalt ions are incorporated into the framework of the catalyst. The catalysts used in this invention, on the other hand, employ non-framework manganese or other metallic ions. This approach permits the preparation of catalysts that are less expensive in that they do not require specialized synthesis but can be prepared by a simple ion exchange process using commercially available zeolites, aluminophosphates, or other suitable materials.

In general, this invention comprises a process for the oxidation of hydrocarbons comprising contacting the hydrocarbon with an oxygen-containing gas in the presence of a catalyst comprising a microporous solid support having from 8- to 12-ring open windows and comprising non-framework metal cations selected from manganese, iron, cobalt, vanadium, chromium, copper, nickel, and ruthenium, and mixtures thereof, providing that the oxygen-containing gas does not contain significant amounts of added hydrogen.

In one preferred embodiment, the invention comprises a process for oxidation of straight or branched-chain alkanes to form a product comprising one or more of terminal alcohols, aldehydes, carboxylic acids, and ketones comprising contacting the alkane with a catalyst comprising a microporous solid support having 10-ring open windows and comprising non-framework metal cations selected from manganese, iron, cobalt, vanadium, chromium, copper, nickel, and ruthenium, and mixtures thereof, providing that the oxygen-containing gas does not contain significant amounts of added hydrogen.

In another embodiment the invention comprises a process for oxidation of cyclic saturated or unsaturated hydrocarbons to form a product comprising the corresponding alcohol or ketone, comprising contacting the hydrocarbon with an oxygen-containing gas in the presence of a catalyst comprising a microporous solid support having from 8- to 12-ring open windows and comprising non-framework metal cations selected from manganese, iron, cobalt, vanadium, chromium, copper, nickel, and ruthenium, and mixtures thereof, providing that the oxygen-containing gas does not contain significant amounts of added hydrogen.

In yet another embodiment the invention comprise a process for selectively oxidizing a para-dialkylbenzene to form a product comprising one or more oxygenated derivatives thereof comprising contacting the dialkylbenzene with a catalyst comprising a microporous solid support having 10-ring open windows and comprising non-framework metal cations selected from manganese, iron, cobalt, vanadium, chromium, copper, nickel, and ruthenium, and mixtures thereof, providing that the oxygen-containing gas does not contain significant amounts of added hydrogen.

In another aspect the invention comprises an oxidation catalyst comprising a microporous solid support having 10-ring open windows, comprising from about 0.01 to about 20 wt. %, preferably from about 0.1 to about 10 wt. %, most preferably from about 0.5 to about 5 wt. %, of non-framework manganese cations.

The process and catalysts of this invention are suitable for oxidation of numerous hydrocarbons in general, including alkanes, cycloalkanes, benzene and alkylbenzenes and, in preferred embodiments, for the terminal regioselective oxidation of alkanes (most preferably straight-chain alkanes) and for selective oxidation of a para-di(lower alkyl)benzene in a mixture of di(lower alkyl)benzenes.

By "alkanes" is meant saturated aliphatic straight- or branched-chain hydrocarbons. Alkanes for which this process is suitable have from 2 to 24 carbon atoms. Preferably the alkanes for which this process is used have from 3 to 12 carbon atoms, most preferably from 5 to 10 carbon atoms, and are most preferably straight-chain compounds. Examples of alkanes include ethane, propane, n-butane, isobutane, n-pentane, isopentane, 2,2-dimethylpropane, n-hexane, n-octane, n-decane and n-dodecane. Typically, in present practices, oxidation of alkanes produces primarily products that are oxidized at an intermediate carbon atom, e.g. isopropanol from propane, sec.-butanol from butane, 2- or 3-octanol from n-octane, etc. However, by use of this invention, including selection of an appropriate catalyst and of process conditions, the proportion of terminally oxidized products can be increased, so as to produce, for example, increased quantities of n-propanol, n-butanol, n-octanol, etc. from the corresponding alkane.

The invention is also suitable for the oxidation of certain cycloalkanes and alkyl-substituted cycloalkanes. Cycloalkanes are cyclical analogs of alkanes, i.e., cyclic saturated aliphatic hydrocarbons having (in the case of the present invention) from 5 to 8 carbon atoms, including cyclopentane, cyclohexane and cyclooctane. Here, of course, terminally regioselective oxidation is not possible due to the cyclic nature of the starting compound, and the product of oxidation of an unsubstituted cycloalkane will be, e.g. cyclohexanol, clycohexanone, etc. The cycloalkanes may be substituted by one or more lower alkyl groups, preferably one or more methyl groups and include, e.g., methylcyclohexane, which can be converted to cyclohexyl methanol and cyclohexane carboxylic acid, useful as chemical intermediates in a number of processes. By "lower alkyl" is meant alkyl groups having from 1 to 4 carbon atoms.

The invention is also suitable for the oxidation of benzene to produce phenol, and for the oxidation of alkylbenzenes to produce corresponding alcohols, aldehydes, and carboxylic acids, for example, oxidation of toluene to produce benzoic acid, benzaldehyde and/or benzyl alcohol. In a preferred embodiment the invention is suitable for the indirect separation of para-di(lower alkyl)benzenes from isomeric mixtures of dialkylbenzenes by selectively oxidizing the para-compounds to oxygenated derivatives, which can then be separated from the reaction products and used as desired. The three xylenes (ortho-, meta- and para-xylene) are difficult to separate; however, the mono-oxygenated or para-dioxygenated derivatives are readily separable from the ortho- and meta-xylenes themselves. Thus, the invention may be used for the effective separation of p-xylene from an isomeric mixture of xylenes through selective oxidation of the p-xylene using a catalyst of the invention that includes a zeolite or other microporous support having 10-ring open windows, into which the para-xylene molecule can diffuse, while the other xylenes are too bulky to diffuse readily through the porous structure. Selective oxidation of para-xylene can then occur in the zeolite structure by contact with the metallic ions present there. For the purposes of this aspect of the invention, it may be sufficient to add a single oxygen atom to the para-xylene to form, for instance, a mono-oxidized product such as 4-methyl benzyl alcohol. However further oxidized products such as 4-methyl benzoic acid and terephthalic acid may be produced. The oxidized p-xylenes may be recovered from the zeolite after completion of the reaction or may be readily separated from the reaction products. In operating this type of process, it may be necessary to selectivate or passivate the catalyst as known in the art, for example as described in U.S. Pat. Nos. 4,097,543 and 5,633,417, so as to increase the selectivity for oxidation of the faster diffusing reactant, which may be done either before or after addition of the non-framework metal ions Similarly, the invention can be used for indirect separation of other para-di(lower alkyl)benzenes from isomeric mixtures by selective oxidation, for example, para-diethyl benzene from an isomeric diethylbenzene mixture, etc.

Terminal regioselective oxidation is accomplished partly through the fact that the catalysts of the invention comprise a microporous solid support having from 8- to 12-ring open windows. As is standard in the art, the term "microporous" refers to solids having a pore diameter of from about 0.25 to about 2 nm. As has been found by some researchers, such as those mentioned in the introductory portion of this Application, such supports contain structures into which straight chain alkanes may diffuse and will fit, so as to expose the terminal portion of the molecule to the metal ions that have been included in the zeolite catalyst. Suitable supports include zeolites, preferably aluminosilicates such as Zeolite A, ZSM-5, ZSM-11, ZSM-57, SSZ35, ITQ-9, ITQ-3, ZSM-23, and ZSM-22, with ZSM-5 being most preferred for regioselective oxidation. The Si/Al ratio of aluminosilicate zeolites usable in this invention can be from 1 to 100. Also usable are zeolites that contain other framework metals such as vanadium, e.g. zeolites VS-1 and VS-2. Zeolites may also contain alkali or alkaline earth metals such as sodium, potassium, calcium, and magnesium. Other suitable non-zeolite supports include aluminophosphates (AlPO materials) having 8-10-ring windows.

The metal cations that are included in the catalysts of the invention are non-framework cations, that is, they were not used in the construction and synthesis of the zeolite or other support, but were subsequently incorporated in it. Incorporation of metal cations into the zeolites is done by an ion exchange method, such as solid state ion exchange, vapor deposition, or liquid phase ion exchange. Suitable metal cations for use in the invention include manganese ($Mn^{+2, +3}$), iron ($Fe^{+2,+3}$), cobalt ($Co^{+2,+3}$), vanadium ($V^{+3,+4,+5}$), chromium ($Cr^{+3,+6}$), copper ($Cu^{+1,+2}$), nickel ($Ni^{+1,+2}$), ruthenium ($Ru^{+2,+3,+4,+6}$), and mixtures thereof, with manganese being preferred. Loading of the metal cation on the support is generally from about 0.01 to about 20 wt. %, preferably from about 0.1 to about 10 wt. %, most preferably from about 0.5 to about 5 wt. %.

The oxidation process of the invention employs an oxygen-containing gas. The oxygen-containing gas used in the process may be in the form of molecular oxygen, a commercial mixture of molecular oxygen with an inert gas such as nitrogen, oxygen-enriched air, or air, but is preferably a commercial gas mixture that contains oxygen. For use in the processes of this invention, the oxygen-containing gas should be one that does not contain significant amounts of added hydrogen. By the latter term is meant that the oxygen-containing gas may contain intrinsic amounts of hydrogen, for example the hydrogen normally present in air, if air is used in the process. However this process does not extend to the use of hydrogen peroxide as an oxidant. Thus it does not include the use of oxygen-containing gases to which significant amounts of hydrogen have been added, i.e. processes in which significant quantities of hydrogen peroxide could conceivably be formed from hydrogen and oxygen in the presence of some metal cations.

In general, the processes of the invention are performed at a temperature of from about room temperature to about 500° C., preferably from about 100 to about 350° C. and a pressure of from about 1 to about 100 atm, preferably from about 10 to about 30 atm. Depending on the feed, products, and other considerations it may be run either in the liquid phase or in the gaseous phase. The catalyst may be employed as convenient, in a single bed or a plurality of beds, and may be used as a fixed bed, fluidized bed or moving bed catalyst. The process can be run as a batch or continuous process, and preferably is run as a continuous process.

The process and catalysts of this invention may be used in reaction systems ranging from large commercial systems for the production of bulk petrochemical chemical products to smaller systems for the production of specialty chemicals. The reaction systems will contain appropriate controls and means for introducing feed, recovering products, recycling unreacted starting materials, and the like. The desired reaction products may be recovered as such and used or sold as appropriate. In many cases the products will be chemical intermediates designed for use in one or more downstream process units at the same location, in which case they may be piped to such units. In other cases the products will be shipped offsite for use at another location, or sold as intermediates.

If a zeolite having 8-ring open windows is used as the catalyst, then, as is known in the art, the inorganic catalyst may have to be dissolved or otherwise destroyed so that the products can be recovered. This may also be necessary for 10-ring open window zeolites if the reaction products are too bulky for ready removal. In other cases the products will not be entrapped in the zeolite structure and can readily be removed via diffusive processes, as known in the art.

In one embodiment of the invention, it has been found that effective activity (in terms of time) of the catalyst may be enhanced by the admixture of it with from about 0.1 to about 100 weight percent of any H-zeolite having larger than 8-ring open windows. While not being bound by any explanation, the H-zeolite is believed to produce this effect by scavenging peroxides formed via oxidation of the hydrocarbon. A similar effect can be achieved by only partially neutralizing acid sites in a support, for example in a zeolite, so that remaining acidic sites can carry out the enhancement function.

EXAMPLES

The following are representative examples of the invention. However, they are only examples; they are not intended to be limiting features of the invention.

Synthesis of Catalysts

Catalysts used in the experiments comprised the zeolites ZSM-5, ZSM-35, ZSM-57, ZSM-58 and mordenite. ZSM-5, ZSM-35 and ZSM-57 are representative of catalyst supports of the invention insofar as selective terminal oxidation of alkanes is concerned; ZSM-58 and mordenite are zeolites that are not within the scope of the invention for this particular purpose, but can be useful as supports for other oxidation reactions within the scope of this invention.

$NH_4$-Mordenite (MOR) was obtained from Zeolyst (CBV 21A; $SiO_2/Al_2O_3$=20). $NH_4$-ZSM-5 (MFI) was obtained from ALSI-PENTA Zeolithe GmbH (SM-27; $SiO_2/Al_2O_3$=24). ZSM-58 (DDR) was prepared in Na-form using procedures described in U.S. Pat. No. 4,698,217. The organic template in ZSM-58 was removed by thermal treatment at 803 K in flowing dry air for 10 h (heated linearly from 298 K at 0.167 K $s^{-1}$, the same temperature ramp was used for other thermal treatments except as otherwise indicated elsewhere). Na-ZSM-58 was converted to its $NH_4$ form by stirring in 1.0 M $NH_4NO_3$ (Aldrich, 99.99+% in deionized water, 5 $cm^3$/g-zeolite) for 3 h at ambient temperature and then filtering and washing the recovered solids with deionized water. This exchange procedure was carried out three times. The ammonium form of each zeolite was converted to its H-form by treatment in flowing He at 803 K in for 4 h. ZSM-57 zeolite (MFS) was prepared in Na-form using procedures described in International patent application WO 03029144 A1. Its H-form was synthesized using the same method as that for H-form ZSM-38.

$Mn^{2+}$ cations were exchanged onto each H-zeolite using sublimation methods. Zeolites (2 g) were dehydrated at 573 K for 0.5 h in dynamic vacuum (~$1.3\times10^{-2}$ Pa), cooled to ambient temperature, and mixed with $MnI_2$; the glass container was then sealed under vacuum and heated to 803 K for 10 h. The resulting materials were dispersed in deionized water at 353 K, and HI exchange products were removed by rinsing with deionized water. These Mn-exchanged samples were treated in flowing dry air at 393 K for 2 h and at 803 K for 2 h before catalytic and characterization measurements.

Catalysts that were prepared had the following characteristics:

TABLE 1

Elemental Analysis and BET Data of Synthesized Mn-Zeolite Catalysts.

| No | Zeolites | channel/window (nm) | Si/Al (atomic radio) | Mn/Al* (atomic ratio) | Mn loading (mmol/g) | Micropore volume ($cm^3 g^{-1}$) | BET area ($m^2/g$) |
|---|---|---|---|---|---|---|---|
| 1 | H-mordenite MOR | 0.65× 0.70 0.34× 0.48 | 10 | — | — | 0.206 | 419 |
| 2 | Mn-MOR-3 | | 10 | 0.020 (0.020) | 0.029 | 0.163 | 343 |
| 3 | Mn-MOR-2 | | 10 | 0.040 (0.040) | 0.060 | 0.164 | 344 |
| 4 | Mn-MOR-1 | | 10 | 0.088 (0.083) | 0.093 | 0.165 | 344 |
| 5 | H-ZSM-5 MEL | 0.53× 0.56 0.51× 0.55 | 13 | — | — | 0.112 | 284 |
| 6 | Mn-ZSM-5 | | 13 | 0.088 (0.10) | 0.10 | 0.105 | 266 |
| 7 | H-ZSM-57 MFS | 0.51× 0.54 | 21 | — | — | 0.149 | 267 |
| 8 | MnZSM-57 | | 21 | 0.12 (0.13) | 0.13 | 0.139 | 248 |
| 9 | H-ZSM-58 DDR | 0.36× 0.44 | 66 | — | — | 0.131 | 270 |
| 10 | Mn-ZSM-58 | | 66 | 0.47 (0.52) | 0.11 | 0.131 | 273 |

*numbers in the parenthesis are expected Mn/Al ratio calculated from the amounts of $MnI_2$ added.

Characterization $N_2$ uptakes were measured volumetrically at its normal boiling point (Autosorb 6, Quantachrome) after dehydration at 673 K for 4 h in a dynamic vacuum of ~4 Pa. Micropore volumes and surface areas were estimated calculated using BET methods.

Isotopic exchange of $D_2$ with acidic OH and silanol groups in zeolites was used to determine the number of O—H that remain after exchange. Samples were dehydrated at 0.167 K $s^{-1}$ to 803 K in 1.67 $cm^3 s^{-1}$ dry air within a quartz cell, held for 1 h at 803 K. Then the sample was cooled to ambient temperature, and exposed to flowing 5% $D_2$/Ar (Matheson; 0.67 $cm^3 s^{-1}$) while raising the temperature to 803 K at 0.167 K $s^{-1}$. Intensities at 2-4 amu ($H_2$, HD, and $D_2$), 16-20 (water isotopomers) and 40 (Ar, internal standard) were measured by mass spectrometry (Orion Compact, MKS Instruments) at 12 s intervals. For calibration of $D_2$, the reactant gas was used, and for $H_2$ a 1% $H_2$/Ar mixture was used. The HD response factor was calibrated from the $D_2$ consumption and $H_2$ production and the resulting H and D mole balance for reactions occurring during a $D_2$-OH experiment:

$$D_2+H^* \rightarrow HD+D^*$$

$$HD+H^* \rightarrow H_2+D^*$$

Magic-angle-spinning $^{27}$Al nuclear magnetic resonance spectra were collected with a Bruker 500 spectrometer (11.7 T field) at 14 kHz after hydrating samples at ambient temperature to weaken quadrupole interactions that broaden $^{27}$Al NMR lines. $^{27}$Al spectra were acquired with a 1.1 µs ($\pi$/15 flip angle) pulse width and a 1 s pulse delay. All spectra were referenced to aqueous Al(NO$_3$)$_3$ (0 ppm).

Infrared spectra were measured using a Mattson spectrometer (RS-10000). After dehydrating samples at 803 K in flowing He for 1 h.; spectra were then acquired at 803 K/He atmosphere.

Catalytic Rates and Selectivities: n-Hexane-O$_2$ Reactions

Catalytic oxidation rates and selectivities were measured in a shielded 100 cm$^3$ high-pressure glass reactor by mixing catalysts (1.0 g) with n-hexane ($\geq$99.0%, absolute, Fluka; 25 cm$^3$). Catalysts were transferred into the reactor immediately after treatment in dry air at 803 K for 2 h. 1,2-Dichlorobenzene (0.20 cm$^3$, 99.8%, Fisher Scientific) was used as internal standard. The reactor pressure was increased to 0.3 MPa using O$_2$ (Airgas, UHP) at ambient temperature and the reactor heated to 403 K, which led to a final pressure of 0.7 MPa (0.4 MPa O$_2$ and 0.3 MPa n-hexane) maintained constant by adding O$_2$ as O$_2$ was consumed. Homogeneous oxidation rates were measured in the same manner without a catalyst.

Gas Chromatographic Analysis

The concentrations of reactants, products, and internal standard were measured by gas chromatography (Agilent 6890, equipped with auto-sampler, mass selective and flame ionization detectors) using a DB-WAX capillary column (60 m×0.25 mm×0.5 µm film, Agilent J&W Scientific). Oxidation products, including 3-hexanone, 2-hexanone, hexanal, 3-hexanol, 2-hexanol, 1-hexanol, acetic acid, propionic acid, butyric acid, valeric acid, and hexanoic acid were identified by their fragmentation patterns and retention times using pure compounds. Each sample was analyzed twice, before and after reaction with triphenylphosphine (Ph$_3$P; Fluka, $\geq$98.5%), which converts hexylhydroperoxides quantitatively to the corresponding alcohols. Alcohols (ROH), ketones and aldehyde (R=O), and peroxides (ROOH) were measured from these two chromatograms by assuming that thermal decomposition of any hexylhydroperoxides during chromatography led to equimolar alcohol and ketone (or aldehyde) mixtures for the underivatized samples. C$_2$-C$_5$ acids formed via oxidative C—C bond cleavage of primary ROH and R=O products; they were measured chromatographically and reported here as the number of n-hexane molecules converted to each product. The designation ROOH represents hexylhydroperoxides.

Non-catalytic Homogeneous Oxidation of n-hexane

Figure 1B:
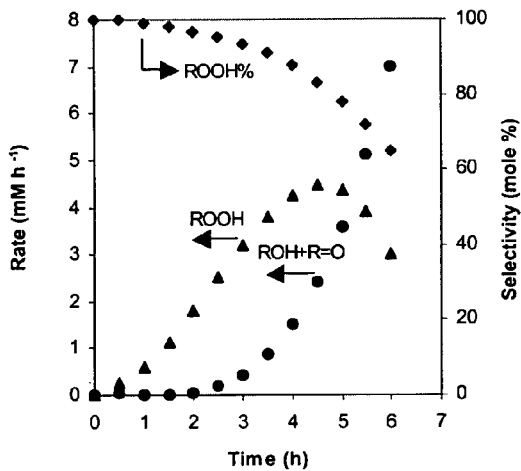

For a comparison, n-hexane oxidation was conducted using oxygen in the absence of a catalyst. The results are shown in FIGS. 1a and 1b. Reaction conditions were: 25 cm$^3$ n-hexane, 0.20 cm$^3$ dichlorobenzene, 403 K, 0.4 MPa O$_2$ and 0.3 MPa n-hexane. Both figures clearly suggest that the homogeneous oxidation of n-hexane experienced an induction period. The formation rate of hexyl peroxide (ROOH) started increasing significantly in 1 h and reached its maximum at about 4.5 h (FIG. 1b). The decrease of the net ROOH formation rate after 5 h indicated that its decomposition was larger than its formation. In comparison with ROOH, the induction period for ROH+R=O (desired oxidation) products was relatively long (about 3 h vs. 1 h of ROOH, FIG. 1b), which is consistent with their formation from ROOH. The terminal selectivity among all ROOH was 8.2% during this initial period.

Catalytic Oxidation of n-hexane on Mn-exchanged Zeolites

Figure 2:
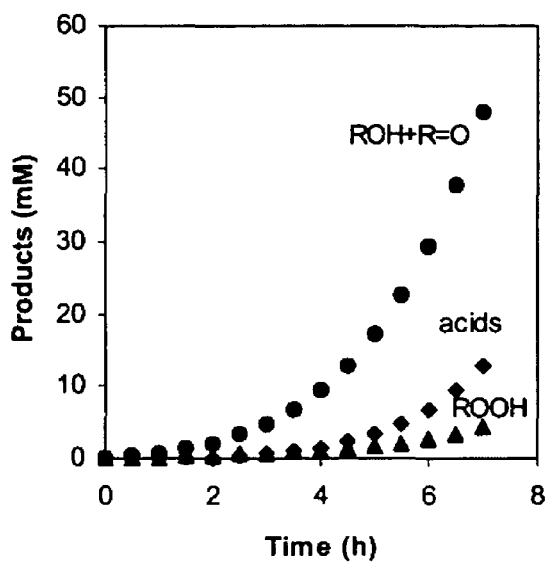
FIG. 2 depicts results of a process according to the invention for oxidation of n-hexane using a catalyst comprising manganese and zeolite ZSM-57.

Catalytic oxidation rates of n-hexane on Mn-exchanged ZSM-57 zeolite are given in FIGS. 2a and 2b. The presence of Mn-ZSM-57 decreases the prevalent ROOH concentrations and induction periods relative to those observed in homogeneous reactions.

Figure 3:
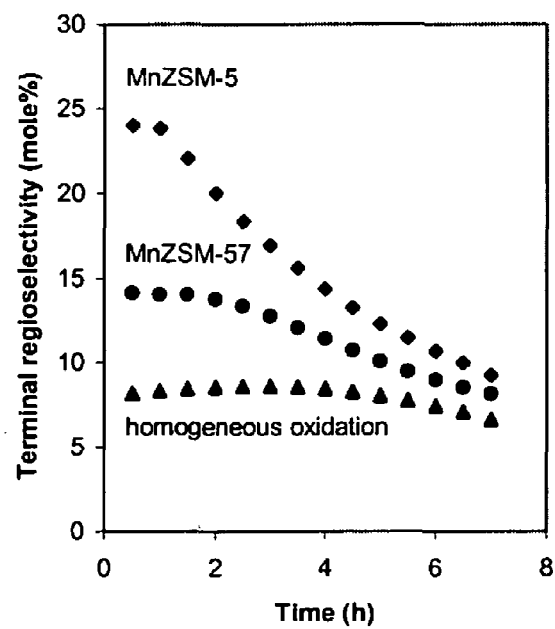
FIG. 3 is a comparison of terminal regioselectivity of n-hexane oxidation without a catalyst, and with two catalysts of the present invention.

FIG. 3 gives the terminal regioselectivity of n-hexane oxidation on Mn-ZSM-5 and Mn-ZSM-57 catalysts as a function of n-hexane conversion (which increases with increased contact time) along with non-catalytic homogeneous oxidation under the same oxidation conditions for comparison. Terminal regioselectivities were ~14% ($k_{prim}/k_{sec}$=0.22) during the early stages (<0.5 h) on Mn-ZSM-57 and 24% ($k_{prim}/k_{sec}$=0.42) on Mn-ZSM-5. These values are much higher than during non-catalytic (8.2%; $k_{prim}/k_{sec}$=0.12) oxidation of n-hexane. Terminal regioselectivities decreased with increasing n-hexane conversion and approached values typical of reaction in non-catalytic media (9.2% after 7 h on Mn-ZSM-5; 8.1% after 7 h on Mn-ZSM-57). A decrease in terminal regioselectivity with increased n-hexane conversion was observed for other Mn-exchanged zeolites in similar experiments, namely Mn-mordenite and Mn-ZSM-58. ZSM-58 has 8-ring open windows; mordenite has 12-ring open windows. They are suitable for use in oxidation catalysts of this invention in general, but are not as suitable for selective terminal oxidation of n-hexane.

These intrinsic terminal selectivities are shown in FIG. 4 for zeolites with different channel/window size and for non-catalytic oxidation experiments, as a comparison. All samples tested except Mn-ZSM-58 showed some preferential terminal oxidation relative to the non-catalytic system, indicating that channel geometry can be used to influence the position of oxygen insertion. Terminal selectivities on 8-ring (ZSM-58: 0.44 nm; 8.4%) and 12-ring (mordenite: 0.70 nm; 9.5%) zeolites were not significantly different for n-hexane than for non-catalytic autoxidation (8.2%). Much higher selectivities were obtained on 10-ring zeolites (ZSM-57: 0.54 nm; 14%; and ZSM-5: 0.56 nm; 24%).

On the other hand, while Mn-zeolites give higher n-hexane oxidation rates than homogeneous systems, in comparative experiments H-zeolites, namely H-mordenite, H-ZSM-57 and H-ZSM-5, gave even lower rates than in the absence of a catalyst. The H-zeolites are thus believed to function as peroxide (ROOH) scavengers. Based on this information an experiment was carried out to ascertain whether some advantage might be obtained by this role of H-zeolites. Oxidation of n-hexane using an Mn-ZSM-5 catalyst was conducted as before. After one hour, the oxidation was stopped and cooled down to room temperature followed by addition of 0.1 g H-ZSM-5. The terminal selectivity vs. reaction time for the resumed reaction was monitored and is given in FIG. 5 along with the sole Mn-ZSM-5 catalyzed reaction. FIG. 5 indicates a reproducible terminal selectivity of ~24% in 1 h for the two separate runs. The terminal selectivity decreased to ~16% during the cooling down, addition of H-ZSM-5, and restarting processes. In fact, the terminal regioselectivity of n-hexane oxidation was then maintained at 16% for 3 h with the presence of H-ZSM-5. This is significantly greater than the sole Mn-ZSM-5 catalyzed oxidation, where the terminal selectivity declined to about 10% at the same contact time (5 h, FIG. 5).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A process for selective oxidation of straight or branched-chain alkanes to produce an oxidation product comprising contacting the alkane in the liquid phase with a catalyst comprising a microporous solid support having 10-ring open windows and comprising non-framework metal cations selected from manganese, iron, cobalt, vanadium, chromium, copper, nickel, and ruthenium, and mixtures thereof, providing that the oxygen-containing gas does not contain significant amounts of added hydrogen, wherein the non-framework metal cations are incorporated into the microporous solid support by vapor deposition methods, and wherein the oxidation product comprises one or more terminal alcohols, terminal aldehydes, terminal carboxylic acids, ketones or combinations thereof, wherein the process is run in a batch mode or a continuous mode utilizing a fixed, fluidized or moving bed catalyst, and wherein the initial terminal regioselectivity is greater than or equal to about 10% and less than or equal to about 24%.

2. A process according to claim 1 in which the hydrocarbon is a straight-chain alkane.

3. A process according to claim 1 in which the hydrocarbon is n-hexane.

4. A process according to claim 1 in which the hydrocarbon is n-octane.

5. A process according to claim 1 in which the support comprises a zeolite.

6. A process according to claim 5 in which the support comprises an aluminosilicate zeolite.

7. A process according to claim 5. in which the zeolite is selected from ZSM-5, ZSM-11, ZSM-57, ITQ-3, ITQ-9, ZSM-23, and SSZ-35.

8. A process according to claim 1 in which the catalyst comprises manganese ions.

9. A process according to claim 1 in which the oxygen-containing gas is air, oxygen, or a commercial mixture of gases containing predominantly oxygen.

10. A process according to claim 1 in which the temperature is from about room temperature to about 500° C.

11. A process according to claim 1 in which the temperature is from about 100 to about 350° C.

12. A process according to claim 1 further in which the oxidation is conducted in the presence of an H-zeolite.

13. A process according to claim 12 in which the H-zeolite is the same zeolite as the zeolite comprised in the catalyst.

14. A process for selectively oxidizing a para-dialkylbenzene to produce an oxidation product comprising contacting the dialkylbenzene in the liquid phase with a catalyst comprising a microporous solid support having 10-ring open windows and comprising non-framework metal cations selected from manganese, iron, cobalt, vanadium, chromium, copper, nickel, ruthenium, and mixtures thereof, providing that the oxygen-containing gas does not contain significant amounts of added hydrogen, wherein the non-framework metal cations are incorporated into the microporous solid support by vapor deposition methods, and wherein the oxidation product comprises one or more terminal alcohols, terminal aldehydes, or terminal carboxylic acids, wherein the process is run in a batch mode or a continuous mode utilizing a fixed, fluidized or moving bed catalyst, and wherein the initial terminal regioselectivity is greater than or equal to about 10% and less than or equal to about 24%.

15. A process according to claim 14 in which the support comprises a zeolite.

16. A process according to claim 15 in which the support comprises an aluminosilicate zeolite.

17. A process according to claim 15 in which the zeolite is selected from ZSM-5, ZSM-11, ZSM-57, ITQ-3, ITQ-9, ZSM-23, and SSZ-35.

18. A process according to claim 14 in which the para-dialkylcylbenzene is para-xylene.

19. A process according to claim 18 in which the feed to the oxidation process comprises an isomeric mixture of xylenes.

20. A process according to claim 19 in which the solid support comprises a zeolite.

21. A process according to claim 20 in which the zeolite is an aluminosilicate zeolite.

22. A process according to claim 20 in which the zeolite is selected from ZSM-5, ZSM-11, ZSM-57, ITQ-9, ZSM-23, and SSZ-35.

23. A process according to claim 14 in which the catalyst comprises manganese ions.

24. A process according to claim 14 in which the oxygen-containing gas is air, oxygen, or a commercial mixture of gases containing predominantly oxygen.

25. A process according to claim 14 in which the temperature is from about room temperature to about 500° C.

26. A process according to claim 14 in which the temperature is from about 100 to about 350° C.

27. A process according to claim 14 further in which the oxidation is conducted in the presence of an H-zeolite.

28. A process according to claim 27 in which the H-zeolite is the same zeolite as the zeolite comprised in the catalyst.

29. An oxidation catalyst for selective oxidation of straight or branched chain alkanes in the liquid phase comprising a microporous solid support having 10-ring open windows, comprising from about 0.01 to about 20 wt. % of non-framework manganese cations wherein the non-framework manganese cations are incorporated into the microporous solid support by vapor deposition methods, and wherein the initial terminal regioselectivity of the catalyst when oxidizing straight or branched chain alkanes is greater than or equal to about 10% and less than or equal to about 24%.

30. An oxidation catalyst according to claim 29 in which the solid support is a zeolite.

31. An oxidation catalyst according to claim 30 in which the solid support is an aluminosilicate zeolite.

32. An oxidation catalyst according to claim 30 in which the zeolite is selected from ZSM-5, ZSM-11, ZSM-57, ITQ-3, ITQ-9, ZSM-23, and SSZ-35.

33. An oxidation catalyst according to claim 29 comprising from about 0.1 to about 10 wt. % manganese cations.

34. An oxidation catalyst according to claim 29 comprising from about 0.5 to about 5 wt. % manganese cations.

35. A method for producing an oxidation catalyst for selective oxidation of straight or branched chain alkanes in the liquid phase comprising providing a microporous solid support having 10-ring open windows, and vapor depositing on the microporous solid support from about 0.01 to about 20 wt.

% of non-framework manganese cations, and wherein the initial terminal regioselectivity of the catalyst when oxidizing straight or branched chain alkanes is greater than or equal to about 10% and less than or equal to about 24%.

36. The method of claim 35, wherein the solid support is a zeolite.

37. The method of claim 36, wherein the solid support is an aluminosilicate zeolite.

38. The method of claim 36, wherein the zeolite is selected from ZSM-5, ZSM-11, ZSM-57, ITQ-3, ITQ-9, ZSM-23, and SSZ-35.

39. The method of claim 35 comprising from about 0.1 to about 10 wt. % of the non-framework manganese cations.

40. The method of claim 35 comprising from about 0.5 to about 5 wt. % of the non-framework manganese cations.

41. The process of claim 1, wherein the initial terminal regioselectivity is greater than or equal to about 14% and less than or equal to about 24%.

42. The process of claim 14, wherein the initial terminal regioselectivity is greater than or equal to about 14% and less than or equal to about 24%.

43. The oxidation catalyst of claim 29, wherein the initial terminal regioselectivity of the catalyst when oxidizing straight or branched chain alkanes is greater than or equal to about 14% and less than or equal to about 24%.

44. The method of claim 35, wherein the initial terminal regioselcctivity of the catalyst when oxidizing straight or branched chain alkanes is greater than or equal to about 14% and less than or equal to about 24%.

* * * * *